(12) United States Patent
Onozawa et al.

(10) Patent No.: US 6,429,325 B1
(45) Date of Patent: Aug. 6, 2002

(54) COPPER MATERIAL FOR CHEMICAL VAPOR DEPOSITION AND PROCESS FOR FORMING THIN FILM USING THE SAME

(75) Inventors: Kazuhisa Onozawa; Toshiya Shingen, both of Tokyo (JP)

(73) Assignee: Asahi Denka Kogyo Kabushiki Kaisha, Tokyo (JP)

( * ) Notice: Subject to any disclaimer, the term of this patent is extended or adjusted under 35 U.S.C. 154(b) by 14 days.

(21) Appl. No.: 09/730,403

(22) Filed: Dec. 6, 2000

(30) Foreign Application Priority Data

Dec. 27, 1999 (JP) ............................. 11-370087

(51) Int. Cl.$^7$ ............................. C07F 1/08; C23G 16/00
(52) U.S. Cl. ........................ 556/40; 556/117; 427/248.1
(58) Field of Search ................. 556/40, 117; 427/248.1

(56) References Cited

U.S. PATENT DOCUMENTS

| | | | | |
|---|---|---|---|---|
| 3,803,242 A | * | 4/1974 | Rothman et al. | 260/595 |
| 3,946,057 A | * | 3/1976 | Reedy | 260/439 R |
| 5,220,044 A | * | 6/1993 | Baum et al. | 556/40 |
| 5,980,983 A | | 11/1999 | Gordon | 427/226 |
| 6,090,964 A | * | 7/2000 | Rhee et al. | 556/117 |
| 6,245,261 B1 | * | 6/2001 | Zhuang et al. | 252/519.2 |
| 6,281,377 B1 | * | 8/2001 | Zhuang et al. | 556/112 |
| 6,340,768 B1 | * | 1/2002 | Welch et al. | 556/12 |

FOREIGN PATENT DOCUMENTS

| | | |
|---|---|---|
| JP | 5132776 | 5/1993 |
| JP | 8186103 | 7/1996 |
| JP | 10140352 | 5/1998 |
| JP | 10195654 | 7/1998 |

* cited by examiner

Primary Examiner—Porfirio Nazario-Gonzalez
(74) Attorney, Agent, or Firm—Young & Thompson

(57) ABSTRACT

A material for chemical vapor deposition comprising a β-diketonatocopper (II) complex which is liquid at room temperature.

3 Claims, 2 Drawing Sheets

COPPER MATERIAL FOR CHEMICAL VAPOR DEPOSITION AND PROCESS FOR FORMING THIN FILM USING THE SAME

BACKGROUND OF THE INVENTION

1. Field of the Invention

The present invention relates to a copper material used for chemical vapor deposition (hereinafter abbreviated as CVD) and a process for forming a copper-containing thin film using the same. More particularly, it relates to a CVD material comprising a β-diketonatocopper (II) complex which is liquid at room temperature and a process for forming a copper-containing thin film using the CVD material.

2. Description of the Related Art

Copper and copper-based alloys have been applied as a wiring material of LSI for their high electrical conductivity and elecromigration resistance. Complex oxides of copper are expected for application as functional ceramic materials, such as high-temperature superconductors.

Techniques for making a copper-containing thin film of copper, copper-containing alloys, complex copper oxides, etc. include sputtering, ion plating, and pyrolytic coating, and the like. In particular, a CVD technique has been given studies as the most suitable thin film formation technique because of superior performance in composition control, step coverage, and planarization and adaptability to the LSI process.

However, the CVD materials that have hitherto been proposed for forming a copper-containing thin film by CVD do not always possess sufficient characteristics. For example, β-diketonatocopper (II) complexes typified by dipivaroylmethanatocopper, being solid, need be gasified through sublimation or be maintained at a high temperature at or above the melting point in the vaporization step. As a result, the amount of vapor produced is insufficient and changes with time, posing problems in raw material gas supply and in-line delivery of the raw material. To solve the problems, a solution CVD method using a solution of a solid material in an organic solvent has been proposed, e.g., in Japanese Patent Laid-Open Nos. 5-132776 and 8-186103. However, the dissolved solid material is likely to precipitate due to temperature change in the vaporization unit, partial volatilization of the solvent or concentration change of the solution. As a result, the feed of the solution tends to decrease with time due to, for example, the precipitate clogging the feed pipe, resulting in instability of film forming rate and film composition.

Japanese Patent Laid-Open Nos. 10-140352 and 10-195654 teach use of a copper compound comprising a β-diketonato complex of copper (I), which is liquid and highly volatile, having added thereto an organosilicon compound. This compound is thermally and chemically labile and decomposes in low temperature and therefore unsuited for use in a multi-component system.

U.S. Pat. No. 5,980,983 discloses use of a liquid β-diketonate material prepared by mixing two or more kinds of β-diketones. Being a mixture, the material is associated with the problems of process instability and precipitation.

SUMMARY OF THE INVENTION

An object of the present invention is to provide a copper material for CVD which is a single liquid compound having stability enough for application to various CVD techniques and a process for forming a copper-containing thin film by CVD using the copper material.

As a result of extensive investigation, the present inventors have discovered a liquid β-diketonatocopper (II) and ascertained that the above object is accomplished by using this compound.

The present invention, having been completed based on the above finding, provides a material for CVD comprising a β-diketonatocopper (II) complex which is liquid at room temperature.

The present invention also provides a process for forming a copper-containing thin film on a substrate by CVD which comprises using the above-described material.

The present invention provides a copper material for CVD which is liquid and has sufficient stability applicable to various CVD techniques and a CVD process for forming a copper-containing thin film using the material.

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
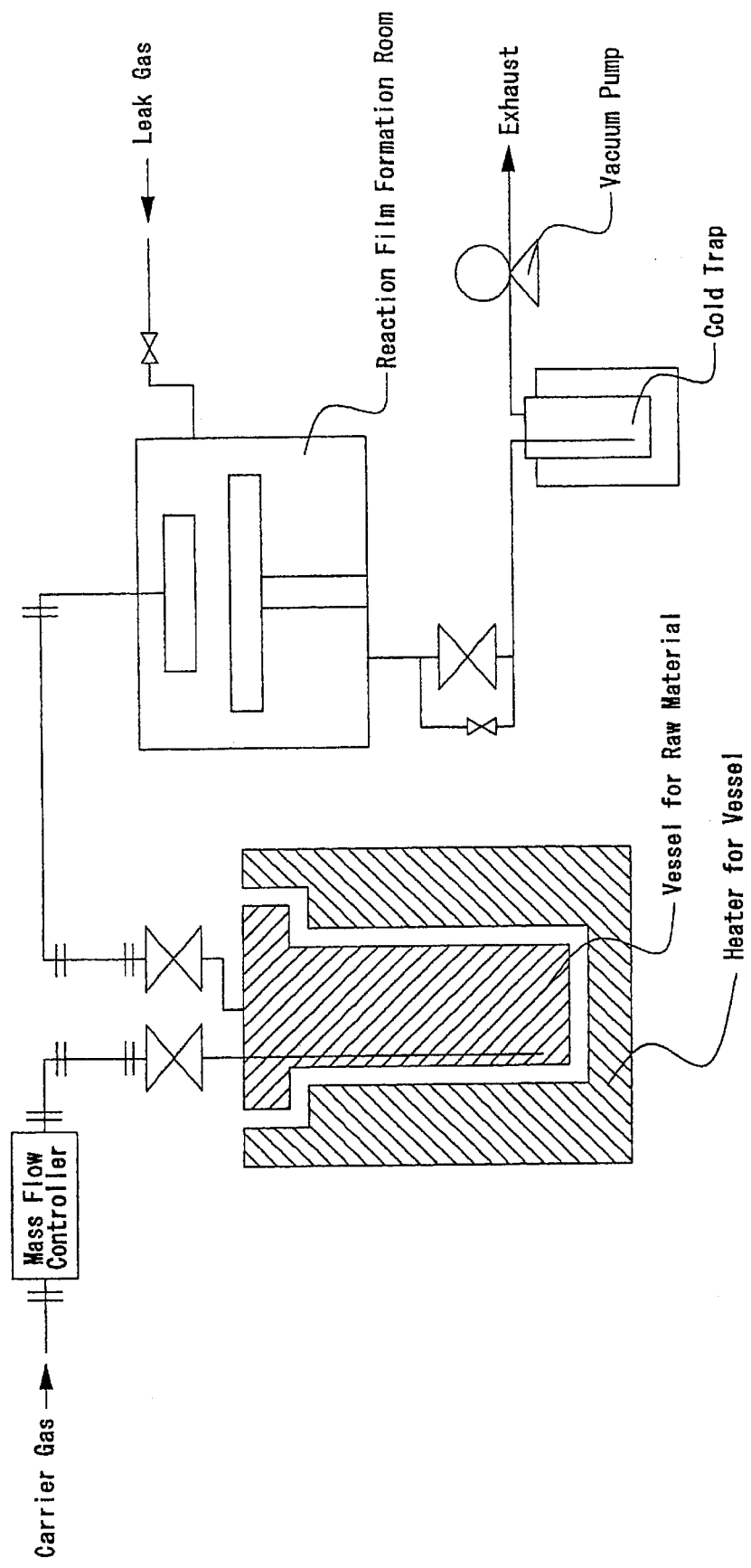
FIG. 1 is a schematic illustration of a CVD apparatus which can be used to carry out the copper-containing thin film formation according to the present invention.

The modes for carrying out the present invention will be described in detail.

The copper material for CVD according to the present invention comprises a β-diketonatocopper (II) complex that is liquid at room temperature. The complex, while liquid, is equal in thermal and chemical stability to known copper materials for CVD comprising solid copper (II) complexes.

Of the β-diketonatocopper (II) complexes of the invention preferred are those represented by formula (I) shown below because, for one thing, β-diketones as a ligand precursor are obtainable with relative ease and, for another, they contain no such elements that might adversely act in thin film deposition, such as halogen elements and a nitrogen element.

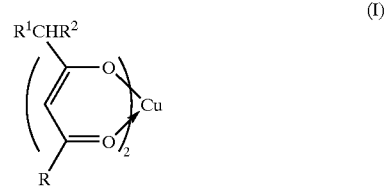

(I)

wherein R represents an isopropyl group or a t-butyl group; $R^1$ represents a methyl group or an ethyl group; and $R^2$ represents a propyl group or a butyl group.

Of the compounds represented by formula (I) still preferred are those represented by formula (II):

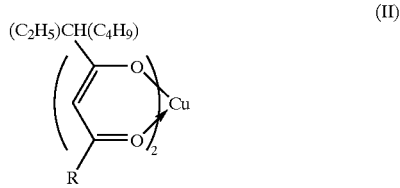

wherein R is as defined above.

The ligand precursor of the complex, i.e., a β-diketone, is obtained by a known condensation reaction between a corresponding ketone and a reactive derivative of an organic acid, such as an ester or an acid halide.

For example, 2-methyl-6-ethyldecane-3,5-dione, which is a ligand precursor of the copper complex wherein R is an isopropyl group, is obtained by condensing isopropyl methyl ketone and phenyl 2-ethylhexanonate, and a ligand precursor in which R is a t-butyl group is obtained similarly from pinacolin and phenyl 2-ethyihexanoate.

The process for preparing the β-diketonato complex of copper (II) of the invention is by no means restricted, and any well-known manner for the reaction between a β-diketone and a copper salt can be employed. For example, the complex can be synthesized from copper (II) hydroxide and a β-diketone.

The term "copper-containing thin film" as used herein denotes a thin film having a composition containing a copper element. Such a composition includes copper, a copper-aluminum alloy, and a copper-silver alloy. Compositions suitable as a high-temperature superconductor include yttrium-barium-copper oxide, lanthanoid-barium-copper oxide, bismuth-strontium-calcium-copper oxide, and thallium-barium-calcium-copper oxide.

The process for forming a copper-containing thin film by CVD according to the present invention is characterized by using the above-mentioned β-diketonatocopper (II) complex as a CVD material. Therefore, known methods for delivering the CVD material, known conditions of film formation, and the like can be applied to the present invention with no particular restrictions.

As for the manner of delivering the CVD material, the complex can be fed alone, or it may be fed in the form of a solution. Solvents used in the latter case are not particularly limited as long as the complex can be dissolved therein sufficiently. Examples of suitable solvents include alcohols such as methanol, ethanol, isopropyl alcohol, and n-butanol; acetic esters such as ethyl acetate, butyl acetate and methoxyethyl acetate; ether alcohols such as methyl cellosolve, ethyl cellosolve, butyl cellosolve, and diethylene glycol monomethyl ether; ethers such as tetrahydrofuran, glyme, diglyme, triglyme, and dibutyl ether; ketones such as methyl butyl ketone, methyl isobutyl ketone, ethyl butyl ketone, dipropyl ketone, diisobutyl ketone, methyl amyl ketone, cyclohexanone, and methylcyclohexanone; and hydrocarbons such as hexane, cyclohexane, methylcyclohexane, ethylcyclohexane, heptane, octane, toluene, and xylene. An appropriate solvent is selected according to the solubility of the complex, the relationship between the working temperature and the boiling point or ignition point of the solvent, and the like. Preferred of the above-enumerated solvents are ethers, such as tetrahydrofuran, glyme, and diglyme, for their stabilizing effects on the complex.

Where the intended copper-containing thin film is of multi-component system, such as an alloy or a complex oxide, a plurality of CVD materials may be vaporized independently and mixed together at the time of film deposition, or they may be vaporized in a mixed-up state.

In carrying out film formation by CVD, including solution CVD using a solution as a CVD material, a nucleophilic reagent is sometimes added to the material or a solution of the material as a stabilizer for the metallic compound (metallic element source) and/or the solution thereof. Since the copper complex of the present invention has high stability, such a stabilizer is not always necessary but can be added, if desired. Stabilizers useful in the present invention include ethylene glycol ethers such as glyme, diglyme, triglyme and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, and 1,1,4,7,10,10-hexamethyltriethylenetetramine; cyclic polyamines such as cyclam and cylene; and β-ketoesters or β-diketones such as methyl acetoacetate, ethyl acetoacetate, and 2-methoxyethyl acetoacetate.

The stabilizer can be used in an amount of 0.1 to 10 mol, preferably 1 to 4 mol, per mole of the CVD material.

The CVD technique which can be used to form the copper-containing thin film of the present invention is not particularly limited as long as it is carried out with general CVD apparatus, including thermal CVD, plasma enhanced CVD, and photo assisted CVD.

In thermal CVD, for instance, the material is vaporized, introduced onto a substrate, and decomposed on the substrate to deposit a copper-containing thin film on the substrate. In order to prevent the material from decomposition in the vaporization step, the material is preferably vaporized under reduced pressure of 100 Torr or less, particularly 50 Torr or less, at or below the decomposition temperature. It is preferred to preheat the substrate to the decomposition temperature of the material or higher, preferably 250° C. or higher, still preferably 350° C. or higher. If desired, the resulting thin film can be subjected to annealing.

The substrate which can be used includes a silicon wafer, ceramics, and glass.

The present invention will now be illustrated in greater detail with reference to Preparation Examples and Examples, but it should be understood that the invention is not construed as being limited thereto.

PREPARATION EXAMPLE 1

Synthesis of Di(2-methyl-6-ethyldecane-3,5-dionato)copper

A 500 ml four-necked flask was charged with 10.0 g of copper (II) hydroxide, 200 g of toluene, and 43.6 g of 2-methyl-6-ethyldecane-3,5-dione, and the mixture was refluxed for 2 hours while removing produced water. The reaction mixture was cooled and filtered through 5C filter paper. The solvent was removed from the filtrate to obtain 47.7 g (yield: 95.7%) of a dark green liquid. The IR absorption spectrum of the liquid of the product showed no peak at 1600 cm$^{-1}$ characteristic of a β-diketone and absorptions at the following wavenumbers which are characteristic of a β-diketonato copper complex: 2958 cm$^{-1}$, 2931 cm$^{-1}$, 2873 cm$^{-1}$, 1558 cm$^{-1}$, 1525 cm$^{-1}$, 1417 cm$^{-1}$, and 451 cm$^{-}$. The copper content measured by ICP analysis was 13.13%, which was in good agreement with the calculated value, 13.07%.

PREPARATION EXAMPLE 2

Synthesis of Di(2,2-dimethyl-6-ethyldecane-3,5-dionato)copper

A 500 ml four-necked flask was charged with 10.0 g of copper (II) hydroxide, 200 g of toluene, and 47.0 g of 2,2,6-trimethylnonane-3,5-dione, and the mixture was refluxed for 2 hours while removing produced water. The reaction mixture was cooled and filtered through 5C filter paper. The solvent was removed from the filtrate to obtain 50.1 g (yield: 95.0%) of a dark green liquid. The IR absorption spectrum of the liquid of the product showed no peak at 1600 cm$^{-1}$ characteristic of a β-diketone and absorptions at the following wavenumbers which are characteristic of a β-diketonato copper complex: 2960 cm$^{-1}$, 2933 cm$^{-}$, 2873 cm$^{-1}$, 1567 cm$^{-}$, 1525 cm$^{-}$, 1427 cm$^{-}$, and 470 cm$^{-}$. The copper content measured by ICP analysis was 12.41%, which was in good agreement with the calculated value, 12.36%.

EXAMPLE 1

Formation of Copper Thin Film by CVD

A copper film was formed on a silicon wafer by use of the CVD system shown in FIG. 1 under the following conditions. The CVD material used was A: di(2,2,6-trimethylnonane-3,5-dionato)copper or B: di(2,2-dimethyl-6-ethyldecane-3,5-dionato)copper. For comparison, C: di(2,2,6-trimethyloctane-3,5-dionato)copper; D: di(2,2-dimethyldecane-3,5-dionato)copper or E: di(2,2-dimethyl-6-ethyloctane-3,5-dionato)copper, which are structurally analogous to the compounds of the present invention but are solid, were used.

CVD Conditions

CVD material temperature: 130° C.

Carrier gas: argon, 90 sccm

Reaction pressure: 4 Torr

Reaction temperature: 450° C.

Film deposition time: 10 minutes

The film formed was annealed in argon at 500° C. for 10 minutes. Ten substrates were successively coated per material, and the change in deposition rate with time was evaluated from the film thickness difference between the first and the tenth samples as measured with a contact type film thickness meter. The film thus formed was confirmed to be copper by X-ray diffractometry. The results obtained are shown in Table 1 immediately below.

TABLE 1

| | First | | Tenth | | Change of | |
|---|---|---|---|---|---|---|
| Material | Film Thickness (nm) | Deposition Rate (nm/min) | Film Thickness (nm) | Deposition Rate (nm/min) | Deposition Rate (nm/min) | Remark |
| A | 98 | 9.8 | 96 | 9.6 | 0.2 | invention |
| B | 93 | 9.3 | 93 | 9.3 | 0.0 | invention |
| C | 85 | 8.5 | 61 | 6.1 | 2.4 | comparison |
| D | 95 | 9.5 | 78 | 7.8 | 1.7 | comparison |
| E | 91 | 9.1 | 70 | 7.0 | 2.1 | comparison |

EXAMPLE 2

Formation of Copper Thin Film by Solution CVD

Figure 2:
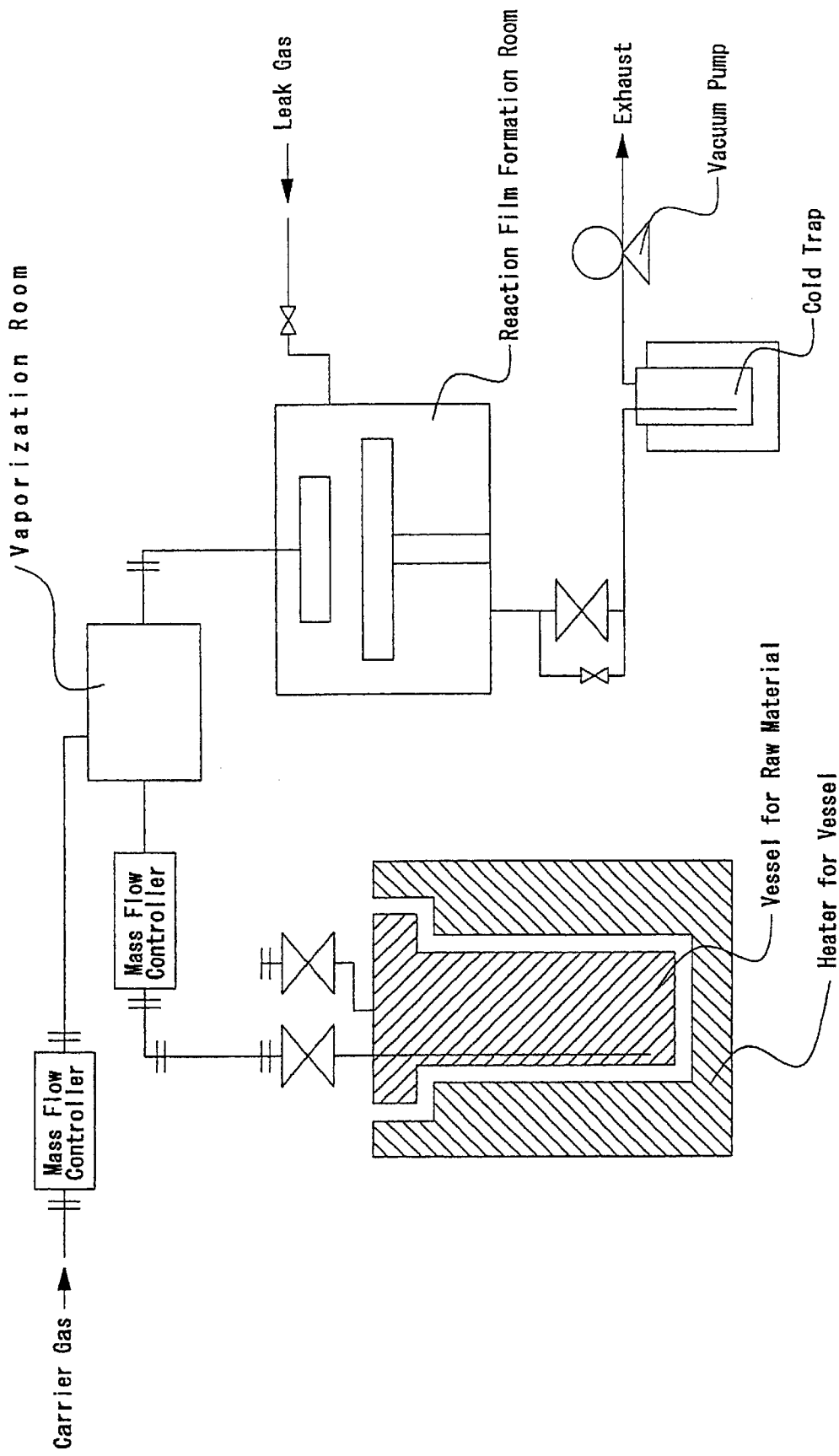
FIG. 2 is a schematic illustration of another CVD apparatus which can be used to carry out the copper-containing thin film formation according to the present invention.

A copper film was formed on a silicon wafer by use of the CVD system shown in FIG. 2 under the following conditions. The CVD material used was A': a 0.2 mol/l solution of di(2,2,6-trimethylnonane-3,5-dionato)copper in tetrahydrofuran (THF) or B': a 0.2 mol/l solution of di(2,2-dimethyl-6-ethyldecane-3,5-dionato)copper in THF. For comparison, a 0.2 mol/l solution of di(2,2,6-trimethyloctane-3,5-dionato)copper, di(2,2-dimethyldecane-3,5-dionato)copper or di(2,2-dimethyl-6-ethyloctane-3,5-dionato)copper, which are structurally analogous to the compounds of the present invention but are solid, in THF (designated C', D' or E', respectively) was used.

CVD Conditions

Vaporization chamber temperature: 200° C.

Flow rate of CVD material: 0.05 ml/min

Carrier gas: argon, 90 sccm

Reaction pressure: 9 Torr

Reaction temperature: 450° C.

Film deposition time: 5 minutes

The film formed was annealed in argon at 500° C. for 10 minutes. Ten substrates were successively coated per material, and the change in deposition rate with time was evaluated from the film thickness difference between the first and the tenth samples as measured with a contact type film thickness meter. The film thus formed was confirmed to be copper by X-ray diffractometry. The results obtained are shown in Table 2 below.

TABLE 2

| | First | | Tenth | | Change of | |
|---|---|---|---|---|---|---|
| Material | Film Thickness (nm) | Deposition Rate (nm/min) | Film Thickness (nm) | Deposition Rate (nm/min) | Deposition Rate (nm/min) | Remark |
| A' | 119 | 23.8 | 116 | 23.2 | 0.6 | invention |
| B' | 117 | 23.4 | 114 | 22.8 | 0.6 | invention |
| C' | 105 | 21.0 | 66 | 13.2 | 7.8 | comparison |
| D' | 116 | 23.2 | 89 | 17.8 | 5.4 | comparison |
| E' | 100 | 20.0 | 70 | 14.0 | 6.2 | comparison |

What is claimed is:

1. A material for chemical vapor deposition comprising a β-diketonatocopper (II) complex which is liquid at room temperature.

2. The material according to claim 1, wherein said β-diketonatocopper (II) complex is represented by formula:

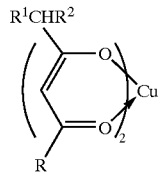

wherein R represents an isopropyl group or a t-butyl group; $R^1$ represents a methyl group or an ethyl group; and $R^2$ represents a propyl group or a butyl group.

3. The material according to claim 2, wherein said β-diketonatocopper (II) complex is represented by formula:

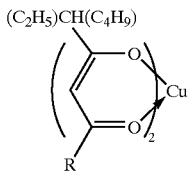

wherein R represents an isopropyl group or a t-butyl group.

* * * * *